United States Patent [19]

Minahan et al.

[11] Patent Number: 5,112,795

[45] Date of Patent: May 12, 1992

[54] SUPPORTED SILVER CATALYST, AND PROCESSES FOR MAKING AND USING SAME

[75] Inventors: David M. Minahan, Cross Lanes; Erlind M. Thorsteinson; Albert C. Liu, both of Charleston, all of W. Va.

[73] Assignee: Union Carbide Chemicals & Plastics Technology Corporation, Danbury, Conn.

[21] Appl. No.: 596,228

[22] Filed: Oct. 12, 1990

[51] Int. Cl.$^5$ .................. B01J 37/02; B01J 23/68; B01J 23/50; B01J 23/89; B01J 23/66; B01J 23/08; B01J 23/10; B01J 23/14

[52] U.S. Cl. .................. 502/324; 502/347; 502/348; 502/330

[58] Field of Search ............ 502/347, 348, 324, 330

[56] References Cited

U.S. PATENT DOCUMENTS

| | | | |
|---|---|---|---|
| 2,605,239 | 7/1952 | Sears | 502/340 |
| 3,563,914 | 2/1971 | Wattimena | 252/463 |
| 3,844,981 | 10/1974 | Cusumane | 502/330 X |
| 3,962,136 | 6/1976 | Nielsen et al. | 252/454 |
| 4,005,049 | 1/1977 | Fields | 502/330 |
| 4,010,115 | 3/1977 | Nielsen et al. | 252/454 |
| 4,012,425 | 3/1977 | Nielsen et al. | 260/348.5 |
| 4,033,903 | 7/1977 | Maxwell | 252/476 |
| 4,066,575 | 1/1978 | Winnick | 252/475 |
| 4,123,385 | 10/1978 | Rebsdat et al. | 502/347 |
| 4,168,247 | 12/1979 | Hayden et al. | 252/476 |
| 4,207,210 | 6/1980 | Kilty | 252/463 |
| 4,248,740 | 2/1981 | Mitsuhata | 252/464 |
| 4,419,276 | 12/1983 | Bhasin et al. | 502/347 |
| 4,455,392 | 6/1984 | Warner et al. | 502/347 |
| 4,820,675 | 4/1989 | Lauritzen | 502/347 X |
| 5,011,809 | 4/1991 | Herzog et al. | 502/348 |

FOREIGN PATENT DOCUMENTS 2002252 2/1979 United Kingdom ............... 502/347

Primary Examiner—W. J. Shine
Assistant Examiner—Douglas J. McGinty
Attorney, Agent, or Firm—Jean B. Mauro

[57] ABSTRACT

A process for preparing a supported silver catalyst for the production of alkylene oxide by the vapor phase oxidation of alkylene with an oxygen-containing gas is disclosed and comprises contacting a silver-contacting support with a solution comprising a metal-containing promoter other than alkali metals or alkaline earth metals. The solution is chosen so that the metal-containing promoter has an increased affinity to the silver-containing carrier relative to its affinity to the carrier without silver. Alkene epoxidation catalysts and alkene epoxidation processes are also disclosed.

49 Claims, No Drawings

SUPPORTED SILVER CATALYST, AND PROCESSES FOR MAKING AND USING SAME

FIELD OF INVENTION

This invention relates to supported silver catalysts for the manufacture of alkylene oxides, preferably ethylene oxide, their preparation, and their use in alkylene oxide, preferably ethylene oxide, processes. More specifically, the invention is concerned with preparing a metal promoted silver catalyst capable of oxidizing an alkene, preferably ethylene, with an oxygen-containing gas in the vapor phase to produce alkylene oxide, preferably ethylene oxide, at high efficiencies.

BACKGROUND OF THE INVENTION

Processes for preparing metal cation-promoted silver catalysts for the production of ethylene oxide are extensively described in the patent literature. The vast majority of these processes employ impregnation techniques wherein solutions containing solubilized compounds of silver and metal cation promoters are used to impregnate a porous carrier or support followed by heat treatment of the impregnated support to effect deposition of the silver and metal cation on the support. Impregnation processes differ from processes for making coated catalysts employ techniques wherein silver and metal-containing promoters are coated onto a catalyst support from an emulsion or slurry followed by a heating step to remove the liquid present from the carrier and effect deposition of the silver and metal-containing promoter. Coated catalysts are generally considered today to be less satisfactory than impregnated catalysts in commercial practice because it is generally believed that coating of silver into the interior surfaces of the carrier and consequently, the coated catalysts are more susceptible to silver loss by mechanical abrasion.

The impregnation methods described in the art for preparing ethylene oxide catalysts include a wide variety of methods of depositing silver and metal cations onto a carrier. These methods are generally distinguished by the process conditions they employ such as low-temperature impregnation, high temperature impregnation, activation in an inert gas atmosphere and/or choice of solvent for the silver impregnating solution.

Impregnation processes are characterized by their employing either a coincidental (or simultaneous) method of depositing silver and metal-containing promoter onto the carrier or a sequential method of addition wherein silver is added either before or after the metal-containing promoter. The addition of silver to a carrier subsequent to the addition of metal-containing promoter is referred to herein as a "metal-first" sequential process of preparation, while the addition of silver to the carrier prior to the addition of the metal-containing promoter is referred to herein as a "silver-first" method of preparation. The coincidental (or simultaneous) addition of silver and metal-containing promoter to a carrier is referred to herein as a "coincidental method" or "coimpregnation method" of preparation. The use of the term "addition" of a metal-containing promoter and/or silver to a carrier is meant to include the steps of impregnating the porous carrier with a solution containing silver and/or metal-containing promoter or precursor thereof, as the case may be, followed by deposition of same upon the carrier, usually by heat treatment.

The comparative performance of catalysts produced by coincidental and sequential methods of impregnation has been reported in the art. Thus, U.S. Pat. No. 3,563,914 to Wattimena and Belgian Patent No. 793,658 and U.S. Pat. Nos. 3,962,136, 4,101,115 and 4,012,425 to Nielsen et al contain comparative data illustrating the relative inefficiency of alkali metal-containing catalysts produced by a silver-first sequential method of addition relative to a coincidental method of addition. U.S. Pat. No. 4,207,210 to Kilty, based upon British specification No. 1 489 335, describes an alkali metal-first process for preparing ethylene oxide catalysts which is said to provide catalysts equivalent or even superior to those produced by coincidental methods of deposition such as set forth in the aforementioned U.S. patents to Nielsen et al.

While other patents in the art directed to silver-first methods of preparing alkali metal-containing catalysts do not provide sufficient data to allow side-by-side comparisons to be made between the coincidental and sequential impregnation processes, nevertheless, the data which are provided appear to indicate that silver-first methods are often the less preferred methods. U.S. Pat. No. 4,033,903 to Maxwell, for example, discloses a silver-first method of addition wherein used ethylene oxide catalysts are reactivated by the addition of an alkali metal-containing promoter to the aged catalyst. The process of the patent is said to be equally effective for enhancing the efficiency of freshly prepared catalysts by employing a heat treatment step intermediate to the steps of silver addition and alkali metal addition to the carrier. The effectiveness of this method of preparation seems somewhat doubtful, however, in view of the data shown in Table III of the patent wherein catalyst R and T, catalysts prepared by a silver-first method are shown to be inferior to catalyst Q, a silver catalyst containing no alkali metal-containing promoter.

U.S. Pat. No. 4,066,575 to Winnick describes a process of catalyst preparation characterized by an activation step wherein the carrier is heated in an inert gas atmosphere following its impregnation with a silver solution. An alkali metal-containing promoter is thereafter deposited on the carrier employing as a solvent for the alkali metal, water or a lower alkanol such as, methanol, ethanol or propanol. Great Britain patent application No. 2,045,636A attempts to distinguish itself from the prior art processes by its low-temperature deposition technique whereby the carrier impregnated with a silver-containing solution is maintained at temperatures below 200° C. prior to the so-called post deposition of alkali metal. The suggested solvents for such post-deposition of alkali metal are water and ethanol. German Offenlegungsschrift No. 2,914,640 discloses a sequential order of impregnation wherein silver is initially applied to the carrier from a suspension and the carrier thereafter immediately dried. Alkali metal is then added to the carrier from a solution using water as the solvent. U.S. Pat. No. 4,248,740 to Mitsuhata et al describes a catalyst preparation procedure employing a silver-first order of addition. The patentees recommend impregnating the carrier with an alkali metal solution containing water or a lower alcohol, such as methanol, ethanol or propanol. The solvent is then catalyst to above 200° C., a critical feature of the described evaporated, care being taken to prevent heating of the process. In U.S. Pat. No. 4,168,247 to Hayden et al, there is described a preparation procedure for catalysts identified by the numbers 34-37 which consists of a silver-first order of addition. The alkali metal-containing promoters were dissolved in water with further addition of methanol, and the resulting solution used to impregnate the carrier.

Japanese patent application No. 142,421/78 (Kokai No. 79,193/79) discloses a "post-treatment" of a used or stabilized silver catalyst by impregnating such catalyst with a solution containing an alkali metal-containing promoter, an organic compound capable of forming a complex salt with silver ion and an alcohol of 1 to 4 carbon atoms. No alcohol other than methanol was used in the impregnating solution described in the examples.

U.S. Pat. No. 4,419,276 to Bhasin et al and U.S. Pat. No. 4,455,392 to Warner et al disclose sequentially preparing ethylene oxide production catalysts by impregnating a carrier with a silver salt and then with a compound of at least one metal-containing promoter. These patents involve the use of certain solvents in at least one of the impregnating solutions. These patents further disclose that the particular metal promoter employed is not critical and may include the one or more alkali metals; one or more alkaline earth metals; or one or more other promoters, such as thallium, gold, tin, antimony, rare earths and the like. The catalysts produced are said to be equally as efficient as catalysts produced by coincidental methods of preparation.

Supported, silver-containing, alkylene oxide catalysts often include one or more metal-containing promoters other than alkali metals or alkaline earth metals to provide enhanced performance, e.g., enhanced activity and/or efficiency and/or stability. It would be advantageous to provide processes to prepare such catalysts, e.g., so as to provide enhanced catalyst preparation processes and/or catalysts and/or alkylene oxide processes which make effective use of such promoters.

In characterizing this invention, the terms "conversion", "selectivity", and "yield" are employed as defined in U.S. Pat. No. 3,420,784, patented Jan. 7, 1969, at column 3, lines 24-35 inclusive. This definition of "selectivity" is consistent with that disclosed in U.S. Pat. No. 2,766,261 at column 6, lines 5-22, and U.S. Pat. No. 3,144,916, lines 58-61. The definitions of "yield" and "conversion" have more varied meaning in the art and are not to be employed as defined, for example, in the aforementioned U.S. Pat. No. 2,766,261. The terms "efficiency" and "selectivity", as used throughout the specification and claims are intended to be synonymous.

SUMMARY OF THE INVENTION

The invention provides processes for preparing supported silver catalysts for the production of alkylene oxide, preferably ethylene oxide, by the vapor phase oxidation of an alkene, preferably ethylene, with an oxygen-containing gas. The catalysts produced by such processes and the use of such silver catalysts for alkylene oxide, preferably ethylene oxide, manufacture are also provided.

In one broad aspect, the present catalyst preparation process comprises contacting a silver-containing support with a solution comprising at least one metal-containing promoter other than alkali metals or alkaline earth metals at conditions sufficient to associate the desired amount of the metal-containing promoter with the silver-containing support to enhance the performance of the catalyst. The contacted support is preferably thereafter treated to effect removal of solvent from the silver-containing support. In one embodiment, the present process preferably provides for, prior to the contacting step, impregnating a catalyst support, in particular a porous catalyst support, with a solution comprising a solvent or a solubilizing agent, and silver salt in an amount sufficient to deposit the desired amount of silver on the support. The impregnated support is then treated to convert at least a fraction of the silver salt to silver metal and effect deposition of silver on the surface of the support. This treated support is then used in the present contacting step.

By properly choosing the contacting solution, for example, the solvent and/or the metal-containing promoter, used to contact the silver-containing catalyst support, new alkylene oxide, preferably ethylene oxide, production catalysts and processes for using such catalysts can be achieved. In addition, such proper choice of solution provides catalyst production advantages.

In one embodiment, the solution is chosen so that the metal-containing promoter included in the solu&ion has an increased affinity to the silver-containing support relative to the affinity of the metal-containing promoter in a similar solution to a similar support without silver. This increased affinity often means that an increased amount of metal-containing promoter is associated with the silver-containing support relative to standard impregnation techniques in which the support is removed from the impregnation solution and has residual impregnation solution filling the pores of the support and this residual liquid is then driven, e.g., evaporated, off leaving only that the metal-containing promoter which was contained in the residual liquid. In such pore-filling impregnations, the bulk of the impregnation solution which is not in the pores of the support and is decanted, filtered or otherwise separated as a liquid from the impregnated support has substantially the same concentration, e.g., within about 10% or about 20%, of metal-containing promoter as the fresh impregnation solution. In contrast, the contacting solutions after use in the present invention often have less than about 75%, preferably less than about 50% and more preferably less than about 30%, of the concentration of metal-containing promoter present in such solution before use in contacting the silver-containing support. In addition, the present contacting step itself and not a subsequent treating step is preferably effective to provide for deposition of the metal-containing promoter on the silver-containing support.

In a particularly useful embodiment, the metal-containing promoter is associated with the silver-containing support at an increased rate relative to the rate at which the metalcontaining promoter is associated with a reference support similar to the silver-containing support but without silver from a similar solution.

The present catalyst preparation process preferably results in selective placement or deposition of the metal-containing promoter on the catalyst, e.g., a disproportionate amount of the metal-containing promoter may be deposited on or near the silver on the surface of the support. Although the final catalyst structure is not clear, nevertheless catalysts prepared according to the present invention are unique and often have very useful catalytic properties, and even enhanced catalytic properties relative to, for example, catalysts having similar compositions but prepared by the coimpregnation or coaddition of silver and metal-containing promoter.

DETAILED DISCUSSION OF THE INVENTION

Alkylene oxides made using the catalysts of this invention are characterized by the structural formula

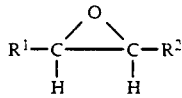

wherein $R^1$ and $R^2$ are lower alkyl, e.g., methyl or ethyl or, preferably, hydrogen. Most preferably the alkylene oxide is ethylene oxide. The alkylene oxides are made from the corresponding alkene, i.e., $R^1HC=CHR^2$. For purposes of ease of understanding, the following discussion will be made with reference to ethylene oxide and ethylene.

As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions.

The supported silver catalysts of this invention are characterized by combining a sufficient amount of at least one metal-containing promoter other than alkali metals or alkaline earth metals to enhance at least one catalytic property, for example, the activity and/or efficiency and/or stability, of the catalyst as compared to a similar catalyst which does not contain the metal-containing promoter. Although the catalysts can be used under widely varying process conditions, for purposes of determining whether sufficient metal-containing promoter has been incorporated into the catalyst, a standard set of process conditions can be used.

The STANDARD ETHYLENE OXIDE PROCESS CONDITIONS (ABBR. "CONDITIONS") for characterizing the catalysts of this invention involve the use of a standard backmixed autoclave with full gas recycle including carbon dioxide. The CONDITIONS may be operated with some variation in ethylene, oxygen and gas phase inhibitor feed. Two cases are illustrated: air process conditions, which simulates in the backmixed reactor the typical conditions employed in commercial air-type ethylene oxide processes where air is used to supply the molecular oxygen and the oxygen process conditions, which simulates in the backmixed reactor the typical conditions in commercial oxygen-type ethylene oxide processes where molecular oxygen, as such, is employed. Each case provides a different efficiency but it is the rule for practically all cases that with air as the oxygen feed, using lower amounts of oxygen and ethylene will yield an efficiency to ethylene oxide which is about 2 to 4 percentage points lower than that when molecular oxygen is employed as oxygen feed. When the catalyst contains a redox-half reaction pair salt and is intended to be used in conjunction with the corresponding efficiency-enhancing gaseous member of a redox-half reaction pair, the CONDITION provide for the presence of such gaseous member. The CONDITIONS employ 2.0 mole % ethylene oxide in the outlet gas of the reactor under the following standard inlet conditions:

| Component | Air process Conditions, Mole % | Oxygen process Conditions, Mole % |
|---|---|---|
| Oxygen | 6.0 | 8.0 |
| Ethylene | 8.0 | 30 |
| Ethane | 0.5 | 0.5 |
| Carbon Dioxide | 6.5 | 6.5 |
| Nitrogen | Balance of Gas | Balance of Gas |
| Parts per million | | |
| ethyl chloride (or one-half such amount when ethylene dichloride is used) | Optimum for Efficiency | Optimum for Efficiency |
| Parts per million | | |
| gaseous member of redox half reaction pair (when required for catalyst) | Optimum for Efficiency | Optimum for Efficiency |

The CONDITIONS employ the well known backmixed bottom-agitated "Magnedrive" autoclaves described in FIG. 2 of the paper by J. M. Berty entitled "Reactor for Vapor Phase-Catalytic Studies", in *Chemical Engineering Progress,* Vol. 70, No. 5, pages 78–84, 1974.

The pressure is maintained constant at 275 psig and the total outlet flow is maintained at 22.6 SCFH. SCFH refers to cubic feet per hour at standard temperature and pressure, namely, 0°C. and one atmosphere. The outlet ethylene oxide concentration is maintained at 2.0% by adjusting the reaction temperature. Thus temperature (°C.) and catalyst efficiency are obtained as the responses describing the catalyst performance.

The catalyst test procedure used in the CONDITIONS involves the following steps:

1. 80 cc of catalyst are charged to the backmixed autoclave. The volume of catalyst is measured in a 1 inch I.D. graduated cylinder after tapping the cylinder several times to thoroughly pack the catalyst. The volume of catalyst is alternatively calculated from the packing density of the carrier and the amount of silver and additives. The weight of the catalyst is noted.

2. The backmixed autoclave is heated to about reaction temperature in a nitrogen flow of 20 SCFH with the fan operating at 1500 rpm. The nitrogen flow is then discontinued and the above-described feed stream is introduced into the reactor. The total gas outlet flow is adjusted to 22.6 SCFH. The temperature is set at 220° C.

3. The temperature is raised over the next three days to 255° C. The selectivity and the activity of the catalyst to ethylene oxide are thus obtained.

The standard deviation of a single test result reporting catalyst efficiency in accordance with the procedure described above is about 0.7% efficiency units. The standard deviation of a single test result reporting catalyst activity in accordance with the procedure described above is about 0.03 mole ethylene oxide. The standard deviation, of course, will depend upon the quality of the equipment and precision of the techniques used in conducting the tests, and thus will vary. The test results reported herein are believed to be within the standard deviation set forth above. The running of a multiplicity of tests will reduce the standard deviation by the square root of the number of tests.

The activity stability and efficiency stability of a catalyst is conveniently determined under the CONDI- TIONS. The rate of decrease in activity and efficiency with time is indicative of the activity stability and efficiency stability of the catalyst. Usually, the study is conducted for about 50 days with a delta ethylene oxide concentration across the catalyst of about 2 mole percent. The time to provide an indication of stability may be 20 or 30 days at ethylene oxide production rates of about 2 mole percent.

The catalyst preparation process of the invention involves contacting a silver-containing catalyst support or carrier with a solution comprising a solvent and at least one metal-containing promoter other than alkali metals or alkaline earth metals at conditions sufficient to associate, preferably deposit and more preferably adsorb, the desired amount of the metal-containing promoter with or on the silver-containing support to enhance the performance of the catalyst. The contacted support is preferably then processed to remove solvent from the contacted support.

As used herein, the term "associate" means that the metal-containing promoter is attached or otherwise joined to the silver-containing catalyst support so that less than about 10%, preferably less than about 5%, of the metal-containing promoter is removed from the contacted support after maintaining a distilled water slurry containing 25% by weight of the contacted support at 25° C. 24 hours. Preferably, the present contacting step effects deposition of the metal-containing promoter on the silver-containing catalyst support. This is in contrast to conventional metal-containing promoter impregnation procedures in which the impregnation solution is used to fill the pores of the support and the pore filled support is then treated, e.g., chemically and/or thermally treated, to effect deposition of the metal-containing promoter on the support. The present contacting step preferably effects deposition of the metal-containing promoter on the silver-containing catalyst support to substantially the same extent as does the conventional pore filling impregnation/treating combination of steps. While not wishing to be limited to any particular theory of operation, it is believed that in more preferred aspects of the invention the metal-containing promoter is adsorbed on the silver-containing catalyst support. Such adsorbed metal-containing promoter is preferably adsorbed to the silver-containing catalyst support so that less than about 5% is removed from the contacted support after maintaining a distilled water slurry containing 25% by weight of the contacted support at 25° C. for 24 hours.

In one embodiment, the contacting solution is chosen so that the metal-containing promoter in the solution has an increased affinity to the silver-containing support relative to the affinity of the promoter in a similar solution to the surface of the support without silver.

In a particularly useful embodiment, the contacting solution is chosen so that the metal-containing promoter is associated with, preferably deposited on and more preferably adsorbed on, the silver-containing support at an increased rate relative to the rate at which the promoter is associated with, preferably deposited on and more preferably adsorbed on, a reference support similar to the support but without silver.

Preferably, prior to the present contacting step, the catalyst support is impregnated with a solution containing a solvent, or a solubilizing agent, and silver salt in an amount sufficient to deposit the desired amount of silver on the support. Thereafter, the silver salt impregnated support is treated to convert at least a fraction of the silver salt to silver metal and effect deposition of silver on the surface of the support. The silver impregnation/treating combination of steps can be repeated more than once, if desired or convenient, to provide the desired amount of silver on the support. Similarly, the present contacting step can be carried out more than once to provide the desired amount of metal-containing promoter in the catalyst. However, since the present contacting step often results in increased amounts of metal-containing promoter being deposited on the silver-containing support, fewer repetitions of the present contacting step may be required, e.g., relative to conventional pore filling impregnation, to achieve the desired catalyst metal-containing promoter concentration. A single contacting may be sufficient.

As noted above, the metal-containing promoter includes a metal other than alkali metals or alkaline earth metals. One or more alkali and/or alkaline earth metals may be included in the solution used in the present contacting step. However, such alkali and/or alkaline earth metals are typically deposited on the silver-containing support by a pore filling impregnation mechanism and substantially not because of the enhanced affinity/increased association rate of the present invention.

The present metal-containing promoters preferably include at least one of the metals of groups 1b, 2b, 3b, 4b, 5b, 6b, 7b and 8 of the Periodic Table, the rare earth metals (lanthanide series), tin, antimony, lead, thallium, bismuth, and mixtures thereof. (References to the Periodic Table herein shall be to that as published by the Chemical Rubber Company, Cleveland, Ohio, In *CRC Handbook of Chemistry and Physics*, 46th Edition, inside back cover.) More preferably, the metal-containing promoter includes at least one of the metals selected from manganese, iron, cobalt, nickel, copper, gold, ruthenium, rhodium, osmium, iridium, zinc, cadmium, the rare earth metals, molybdenum, tungsten, antimony, lead, thallium and mixtures thereof. Manganese and/or cobalt are particularly useful in the metal-containing promoters of the present invention.

The metal-containing promoter or promoters are dissolved in the contacting solution. The promoter metal may be present in a cation, in an anion or in a solvated nonionic compound in the contacting solution. The particular form of the metal-containing promoter employed in the present contacting solution is such as to be soluble in the contacting solution, and to exhibit the increased affinity/association rate of the present invention. Such particular form of the metal-containing promoter may or may not be the actual form of the metal-containing promoter present in the final catalyst. Many of the specific metal-containing promoters identified elsewhere herein may be useful to be included in the present contacting solution.

The concentration of any individual metal-containing promoter in the contacting solution is dependent on a number of factors, for example, the composition of the solution, the specific meta-containing promoter involved, the specific silver-containing support involved and the desired metal-containing promoter content of the fina catalyst. The concentration of metal-containing promoter is preferably chosen so that the desired amount of metal-containing promoter can be included in the final catalyst employing only one contacting step. The solution concentration of the metal-containing promoter may vary over a wide range, preferably in the range of about 0.0001% to about 10% or more, and more preferably about 0.01% to about 5%, calculated as the weight of the metal-containing promoter as the metal based on the total weight of the solution.

As noted above, the metal-containing species present in the contacting solution need not be the promoter metal species present in the final catalyst. The promoter metal-containing species present in the solution is preferably soluble in the solution without the aid of complexing agents which act to complex the metal-containing species, e.g., ion. Such complexed ions often do not provide the desired increased affinity/association rate of the present invention, as described herein.

The solvent useful in the presently useful metal-containing promoter contacting solution may be any suitable solvent provided that it functions as described herein. Thus, the solvent may be water-based, or organic-based, and may be polar or substantially or totally non-polar. In general, the solvent should have sufficient solvating power to solubilize the metal-containing promoter included in the solution. At the same time, it is preferred that the solvent be chosen to avoid having an undue influence on or interaction with, e.g., in terms of coordination coupling with the solvated metal-containing promoter. An overly interactive solvent may reduce the desired increased affinity/association rate of the present invention.

Examples of organic-based solvents include, but are not limited to, alcohols, in particular alkanols; glycols, in particular alkyl glycols; ketones; aldehydes; amines; tetrahydrofuran; nitrobenzene; nitrotoluene; glymes, in particular glyme, diglyme and tetraglyme; and the like. Organic-based solvents which have 1 to about 8 carbon atoms per molecule are preferred.

Mixtures of organic solvents, or of water and one or more organic solvents may be used, provided that such mixed solvents function as desired herein.

In one embodiment, the solution includes a solvent, in particular a substantially or totally non-polar solvent, and the metal-containing promoter is present in the solution in an anion associated with a cation which is complexed to provide for enhanced solubility in the solvent of the salt from which the anion and cation are derived. One particularly useful class of complexing agents which are used to complex such a cation to provide solubility are the crown ethers. These materials are effective to complex the cation, but have substantially no effect, e.g., detrimental influence, on the metal-containing anion.

The present contacting step is conducted at conditions effective to associate or deposit or adsorb the desired amount of metal-containing promoter with or on the silver-containing support to enhance the performance of the final catalyst. Ambient temperature, as well as lower than ambient temperatures and elevated temperatures, may be employed. Elevated temperatures, preferably in the range of about 25° C. to about 80° C. or higher, may be useful, to provide that the metal-containing promoter is soluble in the contacting solution. The contacting preferably occurs at conditions such that substantially all, e.g., at least about 80%, of the contacting solution remains in the liquid phase. Subatmospheric, atmospheric and super atmospheric pressures may be employed. Contacting times may vary widely and are often in the range of about 1 minute to about 24 hours or more.

The present contacting is preferably carried out so that the used contacting solution, i.e., that solution removed from the contacting step as liquid solution after the solution/silver-containing support contacting is completed, has less than about 75%, more preferably less than about 50% and still more preferably less than about 30%, of the concentration of metal-containing promoter present in the contacting solution before the contacting. Catalyst impregnation solutions which rely solely on pore filling to associate the promoter with the support have substantially the same concentration of promoter both before and after the impregnation. The present invention involves more than pore filling to associate the metal-containing promoter with the silver-containing support.

The metal-containing promoter included in the solution may include the metal in an anion or cation. Preferably, the metal present in the solution has an oxidation state which is the highest oxidation state or next to the highest normally accessible oxidation state possible for the particular metal involved. In one useful embodiment, the metal present in solution has an oxidation state of at least $+2$, and more preferably at least $+3$ or higher, for example, permanganate.

The silver solution preferably used to impregnate the support is comprised of a silver salt or compound in a solvent or complexing/solubilizing agent such as the silver solutions disclosed in the art. The particular silver salt employed is not critical and may be chosen, for example, from among silver nitrate, silver oxide or silver carboxylates, such as, silver acetate, oxalate, citrate, phthaate, lactate, propionate, butyrate and higher fatty acid salts.

A wide variety of solvents or complexing/solubilizing agents may be employed to solubilize silver to the desired concentration in the impregnating medium. Generally, the silver concentration in the impregnating medium should be sufficient to deposit on the support from about 2 to about 20 wt. % of silver based on the total weight of the catalyst. Among solvents disclosed in the art as being suitable for this purpose are lactic acid (U.S. Pat. Nos. 2,477,435 to Aries; and 3,501,417 to DeMaio); ammonia (U.S. Pat. No. 2,463,228 to West et al); alcohols, such as ethylene glycol (U.S. Pat. Nos. 2,825,701 to Endler et al; and 3,563,914 to Wattimena); and amines and aqueous mixtures of amines (U.S. Pat. Nos. 2,459,896 to Schwartz; 3,563,914 to Wattimena; 3,702,259 to Nielsen; and 4,097,414 to Cavitt).

Following impregnation of the catalyst carrier or support with silver, the impregnated carrier particles are separated from any remaining non-absorbed solution or slurry. This is conveniently accomplished by draining the excess impregnating medium or alternatively by using separation techniques, such as, filtration or centrifugation. The impregnated carrier is then generally heat treated (e.g., roasted) to effect decomposition and reduction of the silver metal salt to metallic silver. Such roasting may be carried out at a temperature of from about 100° C. to 900° C., preferably from 200° C. to 700° C., for a period of time sufficient to convert substantially all of the silver salt to silver metal. In general, the higher the temperature, the shorter the required reduction period. For example, at a temperature of from about 400° C. to 900° C., reduction may be accomplished in about 1 to 5 minutes. Although a wide range of heating periods have been suggested in the art to thermally treat the impregnated support, (e.g., U.S. Pat. No. 3,563,914 suggests heating for less than 300 seconds to dry but not roast reduce the catalyst; U.S. Pat. No. 3,702,259 discloses heating from 2 to 8 hours at a temperature of from 100° C. to 375° C. to reduce the silver salt in the catalyst; and U.S. Pat. No. 3,962,136 suggests ½ to 8 hours for the same temperature range) it is only important that the reduction time be correlated with temperature such that substantially complete reduction of the silver salt to metal is accomplished. A continuous or step-wise heating program may be used for this purpose.

Contacting the silver-containing support with a solution containing at least one metal-containing promoter other than alkali metals or alkaline earth metals is carried out on a silver-containing support, preferably after silver impregnation and deposition/reduction as described herein. After this contacting, metal-containing promoter support is conveniently separated from any remaining solution, e.g., by draining the excess solution or alternatively by using separation techniques, such as, filtration and centrifugation. The contacted catalyst support is preferably then treated, e.g., dried at ambient or elevated temperature and at ambient or sub-atmospheric pressure, to remove the solvent (or solvents) present and, if necessary, to complete the deposition (with or without decomposition) of the metal-containing promoter on the silver-containing catalyst support. Such treatment may be carried out at a temperature of from about 50° C. to about 900° C., preferably from about 100° C. to about 700 C. and still more preferably from about 200° C. to about 600° C.

This treatment is preferably carried out in air, but a nitrogen, carbon dioxide or hydrogen atmosphere may also be employed. The equipment used for such treatment may use a static or flowing atmosphere of such gases.

The particle size of silver metal deposited upon the carrier is a function of the catalyst preparation procedure employed. Thus, the particular choice of solvent and/or complexing agent, silver salt, heat treatment conditions and catalyst carrier may affect, to varying degrees, the size of the resulting silver particles. For carriers of general interest for the production of ethylene oxide, a distribution of silver particle sizes in the range of 0.05 to 2.0 microns is typically obtained.

The concentration of silver in the finished catalyst may vary from about 2 to 45 or more, often about 2 to 40 or more, weight percent, a commercially preferred range being from about 6% to about 35% by weight of silver. Lower silver concentrations are preferred from an economic standpoint. However, the optimum silver concentration for any particular catalyst will be dependent upon economic factors as well as performance characteristics, such as catalyst efficiency, rate of catalyst aging and reaction temperature.

The optimal amount of the metal-containing promoter or promoters may vary with the particular metal-containing promoter or promoters employed, the effect desired from the metal-containing promoter or promoters, the silver content, the amounts and types of other promoters present and the chemical and physical properties of the support or carrier. However, such metal-containing promoter is often present in an amount of at least 10, preferably at least about 25, ppmw (parts per million by weight) calculated as the weight of the metal in the metal-containing promoter on the total catalyst weight. If too much metal-containing promoter is used, the catalyst performance, e.g., efficiency and/or activity and/or stability, may suffer. If too little metal-containing promoter is present, it is also possible that the performance of the catalyst will suffer or in the amount present will be insufficient to show the desired catalytic effect. In determining desired amounts of metal-containing promoter, a traverse of metal-containing promoter concentrations in the catalyst composition can be effected with the catalysts being evaluated for performance. In some instances, it may be desirable to vary the amounts of other components, e.g., silver and other promoters, to achieve beneficial combinations of effects and optimal catalyst performances. The amount of metal-containing promoter may fall within the range of about 25 to 1000, preferably, about 50 to 500, ppmw calculated as the weight of the metal in the metal-containing promoter and based on the total catalyst weight.

The metal-containing promoter can be provided in various forms, e.g., as a covalent compound such as an oxide, as a cation or as an anion such as a salt, acid or base. The one or more specific species of the metal-containing promoter that provide the desired effect are not certain and may be the component added and/or that generated either during catalyst preparation and/or during use as a cataysт.

Suitable metal-containing promoters include, but are not limited to, metal oxides, metal nitrates, metal nitrites, metal sulfates, metal sulfites, metal carboxylates, e.g., acetates, citrates, lactates, oxalates and the like, metal halides, compounds which contain the promoter metal in an anion, such as oxyanions, metal oxyhalides, metal amine halides, and the like.

Specific examples of metal-containing promoters include, but are not limited to, ferrous oxide, ferric oxide, ferrous nitrate, ferric nitrate, ferrous nitrite, ferric nitrite, ferrous sulfate, ferric sulfate, ferrous acetate, ferric acetate, ferrous citrate, ferric citrate, ferrous lactate, ferric lactate, ferrous oxalate, potassium ferric oxalate, ferric oxalate, ferrous chloride, ferric chloride, ammonium ferrate, cesium ferrate, potassium ferrate, sodium ferrate, nickel (II) oxide, nickel (III) oxide, nickel nitrate, nickel nitrite, nickel sulfate, nickel sulfite, nickel acetate, nickel citrate, nickel lactate, nickel oxalate, nickel chloride, cuprous oxide, cupric oxide, cuprous nitrate, cupric nitrate, cuprous nitrite, cupric nitrite, cuprous sulfate, cupric sulfate, cuprous sulfite, cupric sulfite, cupric acetate, cupric citrate, cupric oxalate, cupric chloride, cuprous chloride, ammoniated ruthenium oxychloride, ruthenium tetroxide, rhodium amine chloride, rhodium trichloride, rhodium sulfate, rhodium sulfite, osmium tetroxide, iridium dichloride, iridium tetrachloride, iridium oxalate, iridium sulfate, cerous oxide, cerous nitrate, cerous chloride, ceric oxide, ceric nitrate, ceric chloride, counterpart compounds for the other lanthanide series rare earths, potassium molybdate, molybdenum nitrate, potassium tungstate, tungsten nitrate, rhenium oxide, rhenium nitrate, rhenium chloride, potassium perrhenate, cesium perrhenate, antimony oxide, antimony nitrate, antimony chloride, gold oxide, gold nitrate, gold chloride, zinc oxide, zinc nitrate, zinc chloride, thallium oxide, thallium nitrate, thallium chloride, lead oxide, lead nitrate, lead sulfate, lead chloride, stannous oxide, stannous nitrate, stannous chloride, stannic oxide, stannous nitrate, stannous chloride, cadmium oxide, cadmium nitrate, cadmium chloride, and the like. Mixtures of promoter metal compounds may be used.

The preferred rare earth metals for use in the present invention are calcium, praseodymium, samarium, terbium, neodymium and mixtures thereof.

One class of metal-containing promoters includes manganese components. In many instances, manganese components can enhance the activity and/or stability of catalysts. The manganese species that provides the enhanced activity and/or stability is not certain and may be the component added or that generated either during catalyst preparation or during use as a catalyst. Manganese components included, but are not limited to, manganese acetate, manganese ammonium sulfate, manganese citrate, manganese dithionate, manganese oxalate, manganous nitrate, manganous sulfate, and manganate anion, e.g., permanganate anion, manganate anion, and the like. When used, the manganese component is often provided in an amount of at least about 1, say, at least about 5, e.g., about 10 to 2000, often about 20 to 1000, ppmw calculated as the weight of manganese based on the total weight of the catalyst.

Another class of metal-containing promoters includes cobalt components. In many instances, cobalt components can enhance the activity and/or efficiency and/or stability of catalysts. The cobalt species that provides the enhanced activity and/or efficiency and/or stability is not certain and may be the component added or that generated either during catalyst preparation or during use as a catalyst. Cobalt components included, but are not limited to, cobaltous oxide, cobaltic oxide, cobaltous nitrate, cobaltic nitrate, cobaltous nitrite, cobaltic nitrite, cobaltous sulfate, cobaltic sulfate cobaltous acetate, cobaltic acetate, cobaltous citrate, cobaltic citrate, cobaltous lactate, cobaltic lactate, cobaltous oxalate, cobaltic oxalate, cobaltous chloride, cobaltic chloride, ammonium cobaltate, cesium cobaltate, potassium cobaltate, sodium cobaltate, and the like. When used, the cobalt component is often provided in an amount of at least about 10 or 20, e.g., about 10 to 1000, preferably about 50 to 500, ppmw calculated as the weight of cobalt based on the total weight of the catalyst.

In any event, each promoter, such as each metal-containing promoter, e.g., whether cationic, anionic or nonionic, is provided on the catalyst in a promoting amount. As used herein the term "promoting amount" of a certain component of a catalyst refers to an amount of that component that works effectively to provide an improvement or enhancement in one or more of the catalytic properties of that catalyst when compared to a catalyst not containing said component. Examples of catalytic properties include, inter alia, operability (resistance to run-away), selectivity, activity, conversion, stability and yield. It is understood by one skilled in the art that one or more of the individual catalytic properties may be enhanced by the "promoting amount" while other catalytic properties may or may not be enhanced or may even be diminished. Indeed, the promoter may enhance efficiency but decrease activity of the catalyst as determined under Standard Ethylene Oxide Process Conditions. It is further understood that different catalytic properties may be enhanced at different operating conditions. For example, a catalyst having enhanced selectivity at one set of operating conditions may be operated at a different set of conditions wherein the improvement shows up in the activity rather than the selectivity and an operator of an ethylene oxide plant will intentionally change the operating conditions in order to take advantage of certain catalytic properties even at the expense of other catalytic properties in order to maximize profits by taking into account feedstock costs, energy costs, by-product removal costs and the like.

The promoting effect provided by the promoters can be affected by a number of variables such as for example, reaction conditions, surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects.

The support or carrier employed in these catalysts in its broadest aspects is selected from the large number of refractory, preferably porous catalyst carriers or support materials which are considered relatively inert in the presence of the ethylene epoxidation feeds, products and reaction conditions. Many such materials are known to persons skilled in the art and may be of natural or synthetic origin and preferably are of a macroporous structure.

The chemical composition of the carrier is not narrowly critical. Carriers may be composed, for example, of alpha-alumina, silicon carbide, silicon dioxide, zirconia, magnesia and various clays. The preferred carriers are alpha-alumina particles often bonded together by a bonding agent and have a very high purity, i.e., at least 98 wt. % alpha-alumina, any remaining components being silica, alkali metal oxides (e.g., sodium oxide) and trace amounts of other metal-containing and/or non-metal-containing additives or impurities; or they may be of lower purity, e.g., about 80 wt. % alpha-alumina, the balance being a mixture of silicon dioxide, various alkali oxides, alkaline earth oxides, iron oxides, and other metal and non-metal oxides. The carriers are formulated so as to be inert under catalyst preparation and reaction conditions. A wide variety of such carriers are commercially available. Alumina carriers are manufactured by United Catalysts, Inc., Louisville, Kentucky, and the Norton Company, Akron, Ohio.

In the case of alpha alumina-containing supports, preference is given to those having a specific surface area as measured by the B.E.T. method of from about 0.03 $m^2/g$ to about 10 $m^2/g$, preferably from about 0.05 $m^2/g$ to about 5 $m^2/g$, more preferably from about 0.1 $m^2/g$ to about 3 $m^2/g$, and a water pore volume as measured by conventional water absorption techniques of from about 0.1 $m^2/g$ to about 0.85 cc/g by volume. The B.E.T. method for determining specific surface area is described in detail in Brunauer, S., Emmet, P. and Teller, E. J. Am. Chem. Soc., 60, 309–16 (1938).

Certain types of alpha alumina-containing supports are particularly preferred. These alpha alumina supports have relatively uniform pore diameters and are more fully characterized by having (1) B.E.T. specific surface areas of from about 0.1 $m^2/g$ to about 3.0 $m^2/g$, preferably about 0.1 $m^2/g$ to about 2.0 $m^2/g$ and (2) water pore volumes of from about 0.10 cc/g to about 0.85 cc/g, preferably from about 0.25 cc/g to about 0.75 cc/g. Median pore diameters for the above-described carriers range from about 0.01 to 100 microns, a more preferred range being from about 0.5 to 50 microns. The carriers may have monomodal, bimodal or multimodal pore distributions. Typical properties of some supports found in the literature are shown in Table I.

TABLE I

| Carrier | A | B | C | D | E | F |
|---|---|---|---|---|---|---|
| B.E.T. Surface Area $m^2/g^{(a)}$ | 0.21 | 0.42 | 0.42 | 0.48 | 0.57 | 2.06 |

TABLE I-continued

| Carrier | A | B | C | D | E | F |
|---|---|---|---|---|---|---|
| Water Pore Volume, cc/g | 0.26 | 0.36 | 0.41 | 0.49 | 0.44 | 0.65 |
| Crush Strength, FPCS, lbs[b] | 100% 20 lbs | 97% 15 | Avg. 21 Range 15-30 | 90% 14 | 90% 15 | No Data |
| Total Pore Volume, Hg. cc/g[c] | 0.26 | 0.42 | 0.42 | 0.46 | 0.42 | 0.65 |
| Average Pore Diameter, Hg. Angstroms[c] | 620 | 560 | 640 | 550 | 770 | 1000 |
| Median Pore Diameter, Hg. microns[c,e] | 3.7 | 2.7 | 3.4 | 3.4 | 2.4 | 2.5 |
| Percent Pore Volume in Pores Greater than 350 Angstroms[c] | 90.0% | 88.5% | 89.5% | 89.1% | 91.5% | 94.1% |
| Percent Pore Volume in Pores Greater than 1 Micron[c] | 87.0% | 82.5% | 83.4% | 82.3% | 83.5% | 61.0% |
| % Wt. Alpha Alumina | 99.5 | 98 | 98.5 | 98.5 | 98 | 70-75 |
| Water Leachable Na, ppmw | 12 | 53 | 21 | 24 | 18 | No Data |
| Acid-Leachable Na, ppmw | 40 | 96 | 87 | 51 | 45 | No Data |
| Water-Leachable K, ppmw | 5 | 22 | 21 | 22 | 10 | No Data |
| Acid-Leachable Fe, ppmw | 2 | 5 | No Data | 1 | 5 | No Data |
| % Wt. SiO$_2$ | .5 | 2 | 1.5 | 15 | 2 | 25-30 |

[a] Method of Brunauer, Emmet and Teller, loc. cit.
[b] Flat Plate Crush Strength, single pellet.
[c] Determined by mercury intrusion to 55,000 psia using Micrometrics Autopore 9200 or 9210 (130° Contact angle, 0.473 N/m surface tension of Hg).
[e] Median pore diameter represents the pore diameter wherein 50% of the total pore volume is found in pores having less than (or greater than) the median pore diameter.

Regardless of the character of the support or carrier used, it is preferably shaped into particles, chunks, pieces, pellets, rings, spheres, wagon wheels, cross-partitioned hollow cylinders (or rings), and the like of a size suitable for employment in fixed bed reactors. Conventional commercial fixed bed ethylene oxide reactors are typically in the form of a plurality of parallel elongated tubes (in a suitable shell) approximately 0.7 to 2.7 inches O.D. and 0.5 to 2.5 inches I.D. and 15-45 feet long filled with catalyst. In such reactors, it is desirable to employ a support formed into a rounded shape, such as, for example, spheres, pellets, rings, cross-partitioned rings, tablets and the like, having diameters from about 0.1 inch to about 0.8 inch.

As with any supported catalyst the optimal performance will depend upon optimizing the carrier in terms of its chemical composition (including impurities), surface area, porosity and pore volume. However, the enhancement in performance provided by this invention may be most pronounced when using less than optimized carriers.

The catalysts of this invention preferably contain, in addition to the metal-containing promoter or promoters, at least one other promoter or modifier to enhance the performance of the catalyst, e.g., to enhance efficiency and/or reduce the burning of ethylene oxide and/or affect activity. These promoters or modifiers are generally provided as chemical compounds.

Frequently, the catalyst contains alkali metal and/or alkaline earth metal as cationic promoter. Exemplary of the alkali meta and/or alkaline earth metals are lithium, sodium, potassium, rubidium, cesium, beryllium, magnesium, calcium, strontium and barium. In some instances, the promoter comprises a mixture of cations, e.g., cesium and at least one other alkali metal, to obtain a synergistic efficiency enhancement as described in British Patent No. 2,043,481 discussed above. The cation promoter may, of course, provide the counter ion to a promoter anion component. Cesium salts alone or in combination with other salts are often used.

In some preferred embodiments of this invention especially when using other than a redox pair catalyst, the amount of leachable potassium cation as determined by leaching in a mineral acid, particularly nitric acid in a concentration of about 10 percent by volume at a temperature of about 90° C. for about 1 hour followed by washing with distilled water, is less than about 50, preferably less than about 25, e.g., 0 to about 25, ppmw based on the weight of the catalyst. Also, in many instances, preferred embodiments of the catalysts of this invention contain less than about 100, e.g., less than about 50, ppmw of leachable sodium cation as determined by the above procedure.

The catalysts of this invention may be of the type comprising at least one efficiency-enhancing salt of a member of a redox-half reaction pair which are intended to be employed in epoxidation processes in which at least one efficiency-enhancing gaseous member of a redox-half reaction pair is present (described hereinbelow). The term "redox-half reaction" is defined herein to mean half-reactions like those found in equations presented in tables of standard reduction or oxidation potentials, also known as standard or single electrode potentials, of the type found in, for instance, "Handbook of Chemistry", N. A. Lange, Editor, McGraw-Hill Book Company, Inc., pages 1213-1218 (1961) or "CRC Handbook of Chemistry and Physics", 65th Edition, CRC Press, Inc., Boca Raton, Fla., pages D155-162 (1984). The term "redox-half reaction pair" refers to the pairs of atoms, molecules or ions or mixtures thereof which undergo oxidation or reduction in such half-reaction equations. Such terms as redox-half reaction pairs are used herein to include those members of the class of substances which provide the desired performance enhancement, rather than a mechanism of the chemistry occurring. Preferably, such compounds, when associated with the catalyst as salts of members of a half reaction pair, are salts in which the anions are oxyanions, preferably an oxyanion of a polyvalent atom; that is, the atom of the anion to which oxygen is bonded is capable of existing, when bonded to a dissimilar atom, in different valence states. Potassium is the preferred cation, although sodium, rubidium and cesium may also be operable, and the preferred anions are nitrate, nitrite and other anions capable of undergoing displacement or other chemical reaction and forming nitrate anions under epoxidation conditions. Preferred salts include $KNO_3$ and $KNO_2$, with $KNO_3$ being most preferred.

The salt of a member of a redox-half reaction pair is added in an amount sufficient to enhance the efficiency of the epoxidation reaction. The precise amount will vary depending upon such variables as the gaseous efficiency-enhancing member of a redox-half reaction used and concentration thereof, the concentration of other components in the gas phase, the amount of silver contained in the catalyst, the surface area of the support, the process conditions, e.g., space velocity and temperature, and morphology of support. Generally, however, a suitable range of concentration of the added efficiency-enhancing salt, calculated as cation, is about 0.01 to about 5 percent, preferably about 0.02 to about 3 percent, by weight, based on the total weight of the catalyst. Most preferably the salt is added in an amount of about 0.03 to about 2 weight percent.

The silver catalysts of the invention are particularly suitable for use in the production of ethylene oxide by the vapor phase oxidation of ethylene with molecular oxygen. The reaction conditions for carrying out the oxidation reaction are well-known and extensively described in the prior art. This applies to reaction conditions, such as temperature, pressure, residence time, concentration of reactants, gas phase diluents (e.g., nitrogen, methane and $CO_2$), gas phase inhibitors (e.g., ethylene chloride and ethylene dichloride), and the like.

The gases fed to the reactor may contain modifiers or inhibitors or additives such as disclosed by Law, et al., in U.S. Pat. Nos. 2,279,469 and 2,279,470, such as nitrogen oxides and nitrogen oxides generating compounds. See also, European Patent No. 3642 which discloses catalysts comprising at least one efficiency-enhancing salt of a redox-half reaction pair in conjunction with at least one gaseous efficiency-enhancing member of a redox-half reaction pair.

The terms "gaseous member of a redox-half reaction pair", "gaseous efficiency-enhancing member of a redox-half reaction pair", or like terms referred to herein have a meaning similar to that for the "salt of a member of a redox-half reaction pair" or like terms, defined above. That is, these terms refer to members of half-reactions, represented in standard or single electrode potential tables in standard reference texts or handbooks which are in a gaseous state and are substances which, in the reaction equations represented in the texts, are either oxidized or reduced. The preferred gaseous efficiency-enhancing materials are compounds containing an element capable of existing in more than two valence states, preferably nitrogen and another element which is, preferably, oxygen. Examples of preferred gaseous efficiency-enhancing members of redox-half reaction pairs include at least one of NO, $NO_2$, $N_2O_3$, $N_2O_4$, $N_2O_5$ or any gaseous substance capable of forming one of the aforementioned gases, particularly NO and $NO_2$, under epoxidation conditions, and mixtures thereof with one or more of $PH_3$, CO, $SO_3$, $SO_2$, $P_2O_5$, and $P_2O_3$. NO is often preferred as the gaseous efficiency-enhancing compound.

Although in some cases it is preferred to employ members of the same half-reaction pair in the reaction system, i.e., both the efficiency-enhancing salt member associated with the catalyst and the gaseous member in the feedstream, as, for example, with a preferred combination of potassium nitrate and nitric oxide, this is not necessary in all cases to achieve satisfactory results. Other combinations, such as $KNO_3/N_2O_3$, $KNO_3/NO_2$, $KNO_3/N_2O_4$, $KNO_3/SO_2$, $KNO_2/NO$, $KNO_2/NO_2$ and $KNO_3$/a mixture of $SO_2$ and NO, may also be employed in the same system. In some instances, the salt and gaseous members may be found in different half-reactions which represent the first and last reactions in a series of half-reaction equations of an overall reaction.

The gaseous efficiency-enhancing member of a redox-half reaction pair is also present in an amount sufficient to enhance the performance, such as the activity of the catalyst, and, particularly, the efficiency of the epoxidation reaction. The precise amount is determined, in part, by the particular efficiency-enhancing salt of a member of a redox-half reaction pair used and the concentration thereof, the particular alkene undergoing oxidation, and by other factors noted above which influence the amount of efficiency-enhancing salt of a member of a redox-half reaction pair. Typically a suitable concentration of the gaseous member of a redox-half reaction pair for epoxidation of most alkenes, including propylene, is about 0.1 to about 2,000 ppm, by volume, of the gaseous feedstream when $N_2$ is used as ballast. When a preferred gaseous member of a redox-half reaction pair, such as NO, is used in the epoxidation of propylene, the preferred concentration is about 2,000 ppm, by volume, with an $N_2$ ballast. However, when ethylene is being oxidized, a suitable concentration is from about 0.1 to about 100 ppm, by volume, of the gaseous feedstream components. Preferably, the gaseous efficiency-enhancing member of a redox-half reaction pair is present in an amount of about 1 to about 80 ppm when about 3 percent, by volume, $CO_2$ is present in the reaction mixture. When nitric oxide is employed as the gaseous efficiency-enhancing compound in an ethylene epoxidation system, it is present in an amount of about 0.1 to about 60 ppm, preferably about 1 to about 40 ppm, when $CO_2$ is present in the reaction mixture, e.g., in amounts up to about 3 volume percent.

The desirability of recycling unreacted feed, or employing a single-pass system, or using successive reactions to increase ethylene conversion by employing reactors in series arrangement can be readily determined by those skilled in the art. The particular mode of operation selected will usually be dictated by process economics.

Generally, the commercially-practiced processes are carried out by continuously introducing a feed stream containing ethylene and oxygen to a catalyst-containing reactor at a temperature of from about 200° C. to 300° C., and a pressure which may vary from about five atmospheres to about 30 atmospheres depending upon the mass velocity and productivity desired. Residence times in large-scale reactors are generally on the order of about 0.1–5 seconds. Oxygen may be supplied to the reaction in an oxygen-containing stream, such as air or as commercial oxygen. The resulting ethylene oxide is separated and recovered from the reaction products using conventional methods. However, for this invention, the ethylene oxide process envisions the normal gas recycle encompassing carbon dioxide recycle in the normal concentrations, e.g., about 0.5 to 6 volume percent.

EXAMPLES

The following examples are by way of illustration only and are not to be construed as limiting the scope of the invention described herein.

The following carrier is employed in certain of the present examples.

CARRIER S

Carrier S is an alpha-alumina carrier prepared by calcining a boehmite-ammonium bifluoride mixture containing 3 weight percent of ammonium bifluoride first at about 600° C. and calcining again at about 1025° C. The chemical and physical properties of the carrier are given below:

| Chemical Composition of Carrier S | |
|---|---|
| alpha-Alumina | 99 wt % |
| Fluoride | 0.25 wt % |
| Water Leachable Impurities | |
| 6 ppm aluminum, 9 ppm calcium, 5 ppm magnesium, 1 ppm potassium, 13 ppm sodium, 36 ppm fluoride, 1 ppm sulfate. | |
| Physical Properties of Carrier S | |
| Surface Area[1] | 1.24 m$^2$/g |
| Pore Volume[2] | 0.77 cc/g |
| Packing Density[3] | 0.50 g/ml |
| Medium Pore Diameter[4] | 1.7 microns |

| Pore Size Distribution, % Total Pore Volume | |
|---|---|
| Pore Size Microns | % Total Pore Volume |
| $P_1$ (<0.1) | 0.5 |
| $P_2$ (0.1-0.5) | 3 |
| $P_3$ (0.5-1.0) | 9.5 |
| $P_4$ (1.0-10) | 81 |
| $P_5$ (10-100) | 2 |
| $P_6$ (>100) | 4 |

[1]Method of Measurement described in "Adsorption Surface Area and Porosity", S. J. Gregg and K. S. W. Sing, Academic Press (1967), pages 316-321.
[2]Method of Measurement as described in ASTM C20-46.
[3]Calculated value based on conventional measurement of the weight of the carrier in a known volume container.
[4]Method of Measurement described in "Application of Mercury Penetration to Materials Analysis", C. Orr, Jr., Powder Technology, Vol. 3, pp. 117-123 (1970).

The identity and amounts of water leachable components of carriers can be determined by any convenient analytical technique. Generally, the carriers are heated in distilled water at a temperature of about 50° C. to 95° C., often 90° C., for about 0.5 to 2, e.g., 1 hour. The liquid is then subject to ion chromatography and inductively Coupled Plasma Spectroscopy Techniques.

SILVER STOCK SOLUTIONS

The silver impregnating solutions used during preparation of the example catalysts presented below are made on a large scale using the following procedure: the indicated amount of ethylenediamine (by weight) is mixed with the initial amount of distilled water. Oxalic acid dihydrate is slowly added such that the exotherm does not cause the temperature of the solution to rise above about 40° C. The indicated amount of silver oxide is added, followed by the monoethanolamine. Distilled water is added to bring the solution to the desired final weight.

| Component (parts by weight) | TYPE A | TYPE B |
|---|---|---|
| ethylenediamine | 11.47 | 11.43 |
| initial water | 20.00 | 24.00 |
| oxalic acid dihydrate | 11.60 | 11.60 |
| silver oxide | 19.82 | 19.82 |
| monoethanolamine | 4.01 | 4.00 |
| add water to final weight of | 71.00 | 75.00 |

EXAMPLES 1-4

The preparation technique for the catalysts of Examples 1 and 2 (comparative) and Examples 3 and 4 is as follows. For the first impregnation, a weighed amount of Carrier S is placed in an impregnation vessel. The vessel is evacuated to about 35 mm-Hg absolute and the desired silver stock solution is added. The solution is allowed to contact the carrier for 15 minutes at atmospheric pressure and is then allowed to drain from the carrier for 15 minutes. The impregnated support is calcined in air on a roaster belt using the following procedure. The first impregnated carrier is spread out in a single layer and transported on a stainless steel belt through a 2 inch by 2 inch square heating zone in 2.5 minutes. Hot air, heated externally by a tubular furnace, is discharged from a port immediately below the belt at about 500° C. at a rate of 66 standard cubic feet per hour per square inch. The roasted carrier is then returned to the impregnation vessel for a second impregnation, which is followed by a second carrier roasting.

In Examples 1 and 2, the solution for the second impregnation also contains the promoters shown in Table 1 below. For Examples 3 and 4, no promoters were added. The second impregnation and second carrier roasting are otherwise carried out in an identical manner to the first impregnation and first carrier roasting described above.

For Examples 3 and 4, a third impregnation step is carried out using an aqueous solution containing the promoters shown in Table 1. The third impregnating step, using the aqueous solution containing the promoters, is followed by a third carrier roasting, both of which steps are otherwise carried out in an identical manner to the first impregnation and first carrier roasting described above.

| | EXAMPLE 1 | EXAMPLE 2 | EXAMPLE 3 | EXAMPLE 4 |
|---|---|---|---|---|
| CARRIER TYPE | S | S | S | S |
| SILVER SOLUTION TYPE | A | A | B | B |
| 1ST IMPREGNATION | | | | |
| Silver Solution, ml. | 130 | 130 | 130 | 130 |
| Carrier Weight, g. | 61.1 | 61.07 | 51.25 | 61.64 |
| 2ND IMPREGNATION | | | | |
| Silver Solution, ml. | 130 | 130 | 130 | 130 |
| KNO3, g. | 1.1254 | 1.0452 | 0 | 0 |
| KMnO4, g. | 0 | 0.1174 | 0 | 0 |
| 3RD IMPREGNATION | | | | |
| Distilled water, ml. | 0 | 0 | 130 | 130 |
| KNO3, g. | 0 | 0 | 1.009 | 1.007 |
| KMnO4, g. | 0 | 0 | 0.1204 | 0.0603 |
| COMPOSITION: | | | | |
| % Silver by Wt. | 35.3 | 33.5 | 33.78 | 33.67 |
| Target ppmw K | 1500 | 1500 | 1500 | 1500 |
| Actual ppmw K | 1405 | 1314 | 1512 | 1471 |
| Target ppmw Mn | 0 | 150 | 150 | 75 |
| Actual ppmw Mn | 0 | 136 | 374 | 188 |

The prepared catalysts are evaluated in standard backmixed bottom agitated "Magnedrive" autoclaves described in FIG. 2 of the paper by J.M. Berty entitled "Reactor for Vapor Phase-Catalytic Studies", in *Chemical Engineering Progress*, Vol 70, No. 5, pages 78–84, 1974. Approximately 80 cc of each catalyst is tested at a nominal gas space velocity of 8000/hr and a pressure of 275 psig. using the following gas feed composition: 8 volume % oxygen, 30 volume % ethylene, about 5 ppmw ethyl chloride, about 5 ppmw nitric oxide and the balance nitrogen. The catalysts are initially operated at 220° C. and the temperature is subsequently raised to a final operating temperature of 255° C. The concentrations of ethyl chloride and nitric oxide are adjusted as necessary to optimize the combination of activity and efficiency. The following performance is observed.

|  | Day 3 Efficiency | Day 21 Efficiency |
| --- | --- | --- |
| Example 1 (comparative) | 84.9% | 85.1% |
| Example 2 (comparative) | 85.1% | 85.2% |
| Example 3 | 83.2% | 86.6% |
| Example 4 | 86.2% | 86.7% |

These results indicate that the catalysts of the present invention in Examples 3 and 4 provide increased efficiencies, particularly after longer periods of time on stream, than do the catalysts of Examples 1 and 2 which are prepared by coimpregnation of silver and manganese. The target values of manganese on the catalyst are based on the impregnating solution merely filling the pores of the carrier. In the coimpregnated catalyst of Example 2, the target manganese concentration is substantially reached. However, in the sequentially impregnated catalysts of Examples 3 and 4, the target manganese concentrations are greatly exceeded. Note further that in all four (4) catalysts, Examples 1 to 4, the target potassium value is substantially reached and not substantially exceeded. This is an indication that the alkali metals and alkaline earth metals do not exhibit the enhanced affinity/association rate of the present invention.

EXAMPLES 5–19

A quantity of silver-containing carrier is prepared in a manner identical to that described in Examples 3 and 4 using Carrier S and Impregnating Solution B in two impregnating steps.

Eight (8) 10 gram lots of this silver-containing carrier are each contacted for one hour with a different aqueous solution containing a particular metal component. The solutions are analyzed for metal content before and after contact. The results are displayed in Table 2.

TABLE 2

| Example | Metal Solution | Concentration (ppmw) in Fresh Solution | Concentration (ppmw) in Solution after 1 hour |
| --- | --- | --- | --- |
| 5 | Manganese as potassium permanganate | 294 | 40.7 |
| 6 | Manganese as manganous nitrate | 293 | 245 |
| 7 | Molybdenum as potassium molybdate | 441 | 360 |
| 8 | Tungsten as potassium tungstate | 337 | 193 |
| 9 | Cobalt as cobaltous nitrate | 346 | 260 |
| 10 | Iron as ferric nitrate | 320 | 226 |
| 11 | Ruthenium as ruthenium trichloride | 357 | 278 |

TABLE 2-continued

| Example | Metal Solution | Concentration (ppmw) in Fresh Solution | Concentration (ppmw) in Solution after 1 hour |
| --- | --- | --- | --- |
| 12 | Rhenium as potassium perrhenate | 360 | 361 |

A further seven (7) 10 gram lots of this silver-containing carrier are each contacted for 24 hours with similar aqueous solutions containing a metal component. The results are displayed in Table 3.

TABLE 3

| Example | Metal Solution | Concentration (ppmw) in Fresh Solution | Concentration (ppmw) in Solution after 24 hours |
| --- | --- | --- | --- |
| 13 | Manganese as potassium permanganate | 300 | 0.75 |
| 14 | Manganese as manganous nitrate | 300 | 180 |
| 15 | Molybdenum as potassium molybdate | 490 | 270 |
| 16 | Tungsten as potassium tungstate | 550 | 12 |
| 17 | Cobalt as cobaltous nitrate | 340 | 230 |
| 18 | Iron as ferric nitrate | 320 | 80 |
| 19 | Rhenium as potassium perrhenate | 320 | 320 |

These results indicate that different components of different metals have different affinities for the silver-containing carrier. In addition, comparing Example 5 and 6, the oxidation state of a particular metal appears to have some influence on the affinity for the silver-containing carrier. Certain metal components, such as potassium perrhenate in Example 12, have little or no increased affinity for the silver-containing carrier.

EXAMPLES 20–25

Four (4) 10 gram lots of the silver-containing carrier produced in Examples 5–19 and 10 grams of the Carrier S are each contacted with an aqueous solution of potassium permanganate for various lengths of time. The potassium permanganate solution is analyzed for manganese before use and then divided into five lots and each was contacted for varying time periods with the silver-containing carrier or the Carrier S. The results are displayed in Table 4.

TABLE 4

| Example | Material Used | Impregnation Time | Concentration (ppm) of Mn in Solution after impregnation |
| --- | --- | --- | --- |
| 20 (Comparative) | Unused Solution | — | 263 |
| 21 (Comparative) | Support S | 24 hours | 221 |
| 22 | Supported Silver | 15 minutes | 51.5 |
| 23 | Supported Silver | 30 minutes | 29.2 |
| 24 | Supported Silver | 6 hours | 1.75 |
| 25 | Supported Silver | 24 hours | 0.75 |

These results indicate that $KMnO_4$ has a much stronger affinity for the silver-containing carrier than for the carrier without silver. Also, this affinity is such that after a relatively short period of time, on the order of 6 hours, substantially all of the manganese is removed from the solution.

While this invention has been described with respect to various specific examples and embodiments, it is to be understood that the invention is not limited thereto and that it can be variously practiced within the scope of the following claims.

We claim:

1. A process for preparing a supported silver catalyst for the production of alkylene oxide by the vapor phase oxidation of alkene with an oxygen containing gas comprising:
   contacting a silver-containing catalyst support with a solution comprising a solvent and at least one metal-containng promoter other than alkali metals or alkaline earth metals at conditions sufficient to associate the desired amount of said metal-containing promoter with said silver-containing catalyst support to enhance the performance of said supported silver catalyst, wherein said solvent does not coordination couple with said metal-containing promoter and said metal-containing promoter in said solution has an increased affinity to said silver-containing catalyst support relative to the affinity of said metal-containing promoter in a similar solution to a similar catalyst support without silver.

2. The process of claim 1 which further comprises removing solvent from said contacted silver-containing catalyst support.

3. The process of claim 2 wherein said removing step is carried out by subjecting said contacted silver-containing catalyst support to an elevated temperature.

4. The process of claim 1 wherein said supported silver catalyst is for the production of ethylene oxide by the vapor phase oxidation of ethylene.

5. The process of claim 1 wherein said metal-containing promoter includes at least one metal selected from the group consisting of the metals of Groups 1b, 2b, 3b, 4b, 5b, 6b, 7b and 8 of the Periodic Table, the rare earth metals, tin, antimony, lead, thallium and bismuth.

6. The process of claim 1 wherein said metal-containing promoter includes at least one metal selected from the group consisting of manganese, iron, cobalt, nickel, copper, gold, ruthenium, rhodium, osmium, iridium, zinc, cadmium, the rare earth metals, molybdenum, tungsten, antimony, lead and thallium.

7. The process of claim 1 wherein said metal-containing promoter includes at least one of manganese and cobalt.

8. The process of claim 1 wherein said silver-containing catalyst support is derived by silver impregnation of a catalyst support.

9. The process of claim 1 wherein said solvent is water-based.

10. The process of claim 1 wherein said solvent is organic-based.

11. The process of claim 1 wherein said support comprises porous alpha-alumina.

12. The process of claim 1 wherein said solvent is substantially non-polar and said metal-containing promoter or precursor thereof is present in said solution in an anion, said anion being associated with a cation which is complexed with said solvent.

13. The process of claim 1 wherein said contacting is effective to deposit said metal-containing promoter on said silver-containing catalyst support.

14. The process of claim 1 wherein said contacting is effective to adsorb said metal-containing promoter on said silver-containing catalyst support.

15. The process of claim 1 said solution after use in said contacting contains less than about 75% of the concentration of said metal-containing promoter present in said solution prior to use in said contacting.

16. A process for preparing a supported silver catalyst for the production of alkylene oxide by the vapor phase oxidation of alkene with an oxygen-containing gas comprising:
   (a) impregnating a catalyst support with a solution comprising a solvent or a solubilizing agent, and silver salt in an amount sufficient to deposit the desired amount of silver on said catalyst support;
   (b) treating said impregnated catalyst support produced in step (a) to convert at least a fraction of the silver salt to silver metal and effect deposition of silver on a portion of the surface of said catalyst support;
   (c) contacting said catalyst support treated in step (b) with a solution comprising a solvent and at least one metal-containing promoter other than alkali metals or alkaline earth metals at 17. The process of claim 16 which further comprises removing solvent from said contacted silver-containing catalyst support.

18. The process of claim 17 wherein said removing step is carried out by subjecting said contacted silver-containing catalyst support to an elevated temperature.

19. The process of claim 16 wherein said supported silver catalyst is for the production of ethylene oxide by the vapor phase oxidation of ethylene.

20. The process of claim 16 wherein said metal-containing promoter includes at least one metal selected from the group consisting of the metals of Groups 1b, 2b, 3b, 4b, 5b, 6b, 7b and 8 of the Periodic Table, the rare earth metals, tin, antimony, lead, thallium, and bismuth.

21. The process of claim 16 wherein said metal-containing promoter includes at least one metal selected from the group consisting of manganese, iron, cobalt, nickel, copper, gold, ruthenium, rhodium, osmium, iridium, zinc, cadmium, the rare earth metals, molybdenum, tungsten, antimony, lead and thallium.

22. The process of claim 16 wherein said metal-containing promoter includes at least one of manganese and cobalt.

23. A process for preparing a supported silver catalyst for the production of alkylene oxide by the vapor phase oxidation of alkene with an oxygen-containing gas comprising:
   contacting a silver-containing support with a solution comprising a solvent and at least one metal-containing promoter other than alkali metals or alkaline earth metals at conditions sufficient to associate the desired amount of said metal-containing promoter with said catalyst support to enhance the performance of said supported silver catalyst, wherein said solvent does not coordination couple with said metal-containing promoter and is chosen so that said metal-containing promoter is associated with said catalyst support at an increased rate relative to the rate at which said metal-containing promoter is associated with a similar catalyst support without silver in a similar solution.

24. The process of claim 23 which further comprises removing solvent from said contacted silver-containing catalyst support.

25. The process of claim 24 wherein said removing step is carried out by subjecting said contacted silver-containing catalyst support to an elevated temperature.

26. The process of claim 23 wherein said supported silver catalyst is for the production of ethylene oxide by the vapor phase oxidation of ethylene.

27. The process of claim 23 wherein said metal-containing promoter includes at least one metal selected from the group consisting of the metals of Groups 1b, 2b, 3b, 4b, 5b, 6b, 7b and 8 of the Periodic Table, the rare earth metals, tin, antimony, lead, thallium and bismuth.

28. The process of claim 23 wherein said metal-containing promoter includes at least one metal selected from the group consisting of manganese, iron, cobalt, nickel, copper, gold, ruthenium, rhodium, osmium, iridium, zinc, cadmium, the rare earth metals, molybdenum, tungsten, antimony, lead and thallium.

29. The process of claim 23 wherein said metal-containing promoter includes at least one of manganese and cobalt.

30. The process of claim 23 wherein said contacting is effective to deposit said metal-containing promoter on said silver-containing catalyst support.

31. The process of claim 23 wherein said contacting is effective to adsorb said metal-containing promoter on said silver-containing catalyst support.

32. The process of claim 23 said solution after use in said contacting contains less than about 75% of the concentration of said metal-containing promoter present in said solution prior to use in said contacting.

33. The process of claim 23 said solution after use in said contacting contains less than about 50% of the concentration of said metal-containing promoter present in said solution prior to use in said contacting.

34. A catalyst for the production of alkylene oxide by the vapor phase oxidation of alkene with an oxygen-containing gas prepared in accordance with the process of claim 1.

35. A catalyst for the production of alkylene oxide by the vapor phase oxidation of alkene with an oxygen-containing gas prepared in accordance with the process of claim 2.

36. A catalyst for the production of ethylene oxide by the vapor phase oxidation of ethylene with an oxygen-containing gas prepared in accordance with the process of claim 5.

37. A catalyst for the production of ethylene oxide by the vapor phase oxidation of ethylene with an oxygen-containing gas prepared in accordance with the process of claim 7.

38. A catalyst for the production of ethylene oxide by the vapor phase oxidation of ethylene with an oxygen-containing gas prepared in accordance with the process of claim 13.

39. A catalyst for the production of ethylene oxide by the vapor phase oxidation of ethylene with an oxygen-containing gas prepared in accordance with the process of claim 15.

40. A catalyst for the production of alkylene oxide by the vapor phase oxidation of alkene with an oxygen-containing gas prepared in accordance with the process of claim 16.

41. A catalyst for the production of alkylene oxide by the vapor phase oxidation of alkene with an oxygen-containing gas prepared in accordance with the process of claim 17.

42. A catalyst for the production of ethylene oxide by the vapor phase oxidation of ethylene with an oxygen-containing gas prepared in accordance with the process of claim 20.

43. A catalyst for the production of ethylene oxide by the vapor phase oxidation of ethylene with an oxygen-containing gas prepared in accordance with the process of claim 22.

44. A catalyst for the production of alkylene oxide by the vapor phase oxidation of alkene with an oxygen-containing gas prepared in accordance with the process of claim 23.

45. A catalyst for the production of alkylene oxide by the vapor phase oxidation of alkene with an oxygen-containing gas prepared in accordance with the process of claim 24.

46. A catalyst for the production of ethylene oxide by the vapor phase oxidation of ethylene with an oxygen-containing gas prepared in accordance with the process of claim 27.

47. A catalyst for the production of ethylene oxide by the vapor phase oxidation of ethylene with an oxygen-containing gas prepared in accordance with the process of claim 28.

48. A catalyst for the production of ethylene oxide by the vapor phase oxidation of ethylene with an oxygen-containing gas prepared in accordance with the process of claim 29.

49. A catalyst for the production of ethylene oxide by the vapor phase oxidation of ethylene with an oxygen-containing gas prepared in accordance with the process of claim 33.

* * * * *

UNITED STATES PATENT AND TRADEMARK OFFICE
CERTIFICATE OF CORRECTION

PATENT NO. : 5,112,795
DATED : May 12, 1992
INVENTOR(S) : Minahan et al.

It is certified that error appears in the above-identified patent and that said Letters Patent is hereby corrected as shown below:

Column 2, line 64, after the word "then", insert "evaporated, care being taken to prevent heating of the".

Column 2, line 65, delete "evaporated, care being taken to prevent heating of the".

Column 4, line 18, delete "solu&ion" and insert "solution".

Column 4, line 50, delete "metalcontaining" and insert "metal-containing".

Column 8, line 62, delete "fina" and insert "final".

Column 12, line 64, delete "calcium" and insert "cerium".

Column 23, line 11, delete "oxygen containing" and insert "oxygen-containing".

Column 24, line 24, after the words "metals at" insert the following: "conditions sufficient to associate the desired amount of said metal-containing promoter with said catalyst support treated in step (b) to enhance the performance of said supported silver catalyst, wherein said solvent does not coordination couple with said metal-containing promoter and said metal-containing promoter in said solution has an increased affinity to said catalyst support treated in step (b) relative to the affinity of said metal-containing promoter in a similar

UNITED STATES PATENT AND TRADEMARK OFFICE
CERTIFICATE OF CORRECTION

Page 2 of 2

PATENT NO. : 5,112,795
DATED : May 12, 1992
INVENTOR(S) : Minahan, et. al.

It is certified that error appears in the above-indentified patent and that said Letters Patent is hereby corrected as shown below:

solution to a similar catalyst support without silver.

Signed and Sealed this

Nineteenth Day of October, 1993

Attest:

BRUCE LEHMAN

*Attesting Officer*     *Commissioner of Patents and Trademarks*